United States Patent [19]
Was

[11] Patent Number: 5,871,211
[45] Date of Patent: Feb. 16, 1999

[54] METHOD AND DEVICE FOR TYPING THINKING STYLES

[76] Inventor: Michael C. Was, 49 E. Summit St., Chargrin Falls, Ohio 44022

[21] Appl. No.: 892,021

[22] Filed: Jul. 14, 1997

[51] Int. Cl.⁶ .................................................. A63F 3/00
[52] U.S. Cl. ............................................................ 273/242
[58] Field of Search ................................... 273/236, 242, 273/243, 248, 249, 429, 430, 431, 432

[56] References Cited

U.S. PATENT DOCUMENTS

| | | |
|---|---|---|
| 3,124,358 | 3/1964 | Weedman . |
| 4,013,294 | 3/1977 | Smeda et al. ........................ 273/243 X |
| 4,124,214 | 11/1978 | Pavis . |
| 4,199,146 | 4/1980 | Dato ......................................... 273/249 |
| 4,216,594 | 8/1980 | Farley et al. ......................... 273/243 X |
| 4,216,971 | 8/1980 | Lyke ......................................... 273/243 |
| 4,635,939 | 1/1987 | Makow ................................... 273/242 |
| 4,682,956 | 7/1987 | Krane . |
| 4,741,539 | 5/1988 | Sutton et al. . |
| 4,815,976 | 3/1989 | Krane ................................... 273/243 X |
| 4,877,254 | 10/1989 | Yuscavage . |
| 4,893,819 | 1/1990 | Wright . |
| 4,923,198 | 5/1990 | Diaz . |
| 4,971,561 | 11/1990 | Krane ................................... 273/243 X |
| 5,156,407 | 10/1992 | Moore . |
| 5,511,982 | 4/1996 | Pigache et al. . |
| 5,516,290 | 5/1996 | Quigley et al. . |
| 5,540,590 | 7/1996 | Avery et al. . |
| 5,542,849 | 8/1996 | Douglass . |
| 5,568,924 | 10/1996 | Katsuren . |
| 5,573,404 | 11/1996 | Stawski, II . |

Primary Examiner—William E. Stoll
Attorney, Agent, or Firm—Greenblum & Bernstein, P.L.C.

[57] ABSTRACT

A method and device for typing thinking styles. More specifically, a group interactive method and device for determining people's thinking style types which they often express in their characteristic traits of temperament and personality. More specifically, a game that is enhanced by group interactions, and in the playing of which an individual person's thinking style may be categorized into one of four distinct classes. Methods and devices of this invention are based on the foundation of a novel model for classifying individuals and groups of people's styles of thinking into four separate categories.

13 Claims, 9 Drawing Sheets

CARD SAMPLES: BEAR CARDS

BEAR QUEST

WHEN GOING ON A LONG HIKE, THE KEY THING IS TO:
A. GO WITH OTHER CAMPERS
B. PLAN AND PACK THE THINGS YOU'LL NEED
C. STAY ALERT TO DANGERS SO YOU DON'T GET HURT
D. ENJOY THE SCENERY AND FIND YOUR WAY BACK (ON BACK)

MOVE A SPACE TOWARD:
A. HEART  C. SPADE
B. CLUB   D. DIAMOND

BEAR QUEST

I HAVE A GOOD DAY AT CAMP WHEN I:
A. DO JUST WHATEVER THE SPIRIT MOVES ME TO DO
B. GO THROUGH MY ORDINARY DAILY ROUTINE
C. HAVE MEANINGFUL TIMES WITH FRIENDS
D. SOLVE A CHALLENGING PROBLEM

MOVE A SPACE TOWARD:
A. DIAMOND C. HEART
B. CLUB     D. SPADE

CARD SAMPLES: OWL CARDS

OWL MISSION
BE A HEART CAMPER

COMPANY MANAGEMENT SHOULD FOCUS ON THE:
A. BOTTOM LINE, FOR BUSINESS DEPENDS ON A RETURN ON INVESTMENT
B. CUSTOMER, FOR BUSINESS DEPENDS ON BUYERS BEING HAPPY AND SATISFIED WITH PRODUCTS (ON BACK)

THE LIKELY *HEART CAMPER* RESPONSE IS B

OWL MISSION
BE A CLUB CAMPER

OUR POLITICIANS SHOULD:
A. END DISCRIMINATION AGAINST ALL MINORITIES AND HOMOSEXUALS
B. PRESERVE SOUND FAMILY VALUES THAT MINIMIZE DISORDER TO WHICH A CHILD IS EXPOSED

THE LIKELY *CLUB CAMPER* RESPONSE IS B

*Fig. 4*

Samples of Owl Camper Badges:
Badges are approximately 2" round
and plastic covered, mounted
on a pin like campaign buttons

GUIDE TO THE FOUR THINKING STYLES

♣ CAMP  STABILIZERS

THOUGHT TYPE: ORDER-SETTING
OPERATIONAL MODE OF ESTABLISHING PROCEDURES AND ROUTINES, PUTTING THINGS IN SEQUENTIAL STEPS (1,2,3...A, B, C), SETTING STANDARDS, RULE-MAKING.

GREATER PURPOSE: ESTABLISH STABILITY
PROVIDE THE BASE OF ORDERLY FOUNDATIONS, CODES, METHODS AND TRADITIONS FOR THE GROUP.

STRENGTHS: RESPONSIBLE, PRECISE
METHODICAL, THOROUGH, ATTEND TO DETAIL AND DISCIPLINE

WEAKNESSES: NEAR FOCUSED
RIGID ON HOW TO'S, RISK ADVERSE, PESSIMISTIC

IDEAL WORK: ABLE TO BE RIGHT
CLEARLY DEFINED, TIME TO DO, EVOKING CORRECTNESS

LANGUAGE KEY: CLOSE
LIMIT, STRUCTURE, ORGANIZE, MAINTAIN, KEEP, STOCK, RULE, STEPS, SCHEDULE, TIME, SAVE, SHOULD, REQUIRE, LAW, JUDGE, CONSCIENCE

PROMINENT EXAMPLES:
BOB DOLE, QUEEN ELIZABETH, G. WASHINGTON

♥ CAMP  UNIFIERS

THOUGHT TYPE: RELATING
OPERATIONAL MODE OF ASSOCIATING, LINKING AND HARMONIZING THOUGHTS, PEOPLE, ETC. WITH EACH OTHER, LAYERING, BUILDING MEANING, ASSEMBLING.

GREATER PURPOSE: BUILD TOGETHERNESS
PROVIDE COHESIVENESS AND TEAM INCLUSIVENESS TO INTERCONNECT GROUP MEMBERS WITH ENVIRONS.

STRENGTHS: PEOPLE SKILLS
COMMUNICATIVE, SUPPORTIVE, LOYAL, CONSISTENT

WEAKNESSES: INDECISIVE
PROCRASTINATING, AVOID CONTROVERSY

IDEAL WORK: VALUED IN GROUP
WORKING WITH PEOPLE, SECURE, MINIMAL CONFLICT

LANGUAGE KEY: CONNECT
UNION, CARE, HARMONY, FLOW, ASSOCIATE, ENGAGE, COMMUNE, TOGETHER, LINK, LOVE, LIKE, WARM, PEACE, EASY, FEEL, GIVE, SOUL

PROMINENT EXAMPLES:
BILL CLINTON, PRINCE CHARLES, MOTHER TERESA

FIG. 6A

♠ CAMP IDENTIFIERS

*THOUGHT TYPE:* ANALYZING
PERCEPTUAL MODE OF SELECTIVELY SEPARATING THINGS INTO PARTS BY LOGIC, ASSIGNING, IDENTIFYING, EVALUATING, DECIDING ON GOALS/COURSE OF ACTION.

*GREATER PURPOSE:* MANAGE OUR REALITY
PROVIDE THE DECISION-MAKING CAPABILITY TO NARROW, CHOOSE AND DEFINE THE GROUP'S PROGRAM.

*STRENGTHS:* PROBLEM SOLVING
DETERMINE GOAL, PERSIST, GET IT DONE, SELF-RELIANT

*WEAKNESSES:* INSENSITIVE, IMPATIENT INFLEXIBLE, DEMANDING OF OTHERS

*IDEAL WORK:* CHALLENGE
INDEPENDENCE, VARIETY, CONTROL, DIRECT ANSWERS

*LANGUAGE KEY:* CUT
DECIDE, QUESTION, PINPOINT, DIRECT, THINK, EVALUATE, DETERMINE, INQUIRE, RESOLVE, CRITICAL, COOL, SEPARATE, ANSWER, GET, EGO

*PROMINENT EXAMPLES:*
NEWT GINGRICH, PRINCE PHILIP, HENRY FORD

♦ CAMP EXPANDERS

*THOUGHT TYPE:* CONCEIVING
PERCEPTUAL MODE OF ENVISIONING POSSIBILITIES, MANIPULATING SYMBOLS HOLISTICALLY, IMAGINING NEW IDEAS OR COURSES OF ACTION, MIND DOODLING.

*GREATER PURPOSE:* DEVELOP NEW FUTURES
PROVIDE BROADER AWARENESS AND INNOVATION WHICH ALLOW THE GROUP TO ADAPT AND GROW.

*STRENGTHS:* IMAGINATIVE
LONG TERM THINKING, CREATIVE, PERCEPTIVE, 'CAN DO' SPIRIT, OPTIMISTIC

*WEAKNESSES:* LOOSE ON PROCEDURES OVER-ESTIMATE, LACK FOLLOW-THROUGH

*IDEAL WORK:* UNCONTROLLED
OPEN TO SPONTANEITY, FREE OF DETAIL, RISK-ENABLING

*LANGUAGE KEY:* OPEN
DREAM, POSSIBLY, COULD, WISH, HOPE, FREE, CREATE, IMAGINE, INSPIRE, SPACE, CANDID, LEAP, GUESS, DEVELOP, GENERATE, GROW, SPIRIT

*PROMINENT EXAMPLES:*
STEVEN SPIELBERG, PRINCESS DIANA, T. JEFFERSON

FIG. 6B

For a record of your experiences here at Camp Paradox, keep a running count of your moves by suit:

METHOD AND DEVICE FOR TYPING THINKING STYLES

BACKGROUND OF THE INVENTION

1. Field of the Invention

This invention relates to a method and device for typing thinking styles. More specifically, this invention relates to a group interactive method and device for determining people's thinking style types which they often express in their characteristic traits of temperament and personality. More specifically, this invention relates to a game that is enhanced by group interactions, and in the playing of which, an individual person's thinking style may be categorized into one of four distinct classes. Methods and devices of this invention are based on the foundation of a novel model for classifying individuals and groups of people's styles of thinking into four separate categories.

2. Background of the Invention and Related Information

Humans have long sought to understand each other's differences in thinking styles. Five centuries before Christ, Hippocrates attempted to improve medical diagnoses by postulating four types of temperaments which he termed: Sanguine, Choleric, Phlegmatic, and Melancholic. Hippocrates ascribed such diversities in the ways people think and behave to varying influences of different bodily fluids. His temperament types, known as the four humors, have been in continual usage until modern science provided better definitions.

For thousands of years Native Americans likewise had their "Medicine Wheel" which oriented four perspectives on life to ordinal compass points around a circle. Each of their four styles were symbolized by animals as follows: the Buffalo (north) represented cool wisdom, the Mouse (south) portrayed innocent trust, the Bear (west) characterized staying in place, and the Eagle (east) illustrated illumination and vision beyond.

With the advent of modern science and medical surgery, research has increasingly traced the causes of people's differences to varying operations in the brain. The work of noted Swiss psychologist Carl Jung in the 1920's and '30s led him to gather that there were four functions of the mind, two pairs opposing each other, which he labeled "Thinking" versus "Feeling" and "Sensation" versus "Intuition." He believed that although people all possess these abilities, one of the four functions dominates a person's personality. Based on the mental functions and attitudes that Jung described, in the 1950s psychologists Isabel Myers and Katherine Briggs developed a personality test, the now widely used Myers-Briggs Type Indicator (MBTI). The MBTI rates people's written responses to questions to measure four sets of opposing characteristics. Each set is a continuum with opposite ends designated by letters which denote the pair's behavioral extremes:

| | | |
|---|---|---|
| Extroversion | E .......................... I | Introversion |
| Sensation | S .......................... N | INtuition |
| Thinking | T .......................... F | Feeling |
| Judging | J .......................... P | Perceiving |

Testing identifies a person's gravitation toward one end or the other of each set of characteristics, and by the combination of which sixteen types of personalities are possible (for example, ESTJ, ISTJ, etc.). With this MBTI method, Jung's concept of a dominant function was lost in the mix, because each of the personality types is indicated by preferences for two functions plus two attitudes.

In the 1960s psycho-biologist Roger Sperry began experiments with people who previously had brain surgery to reduce symptoms of epilepsy. Because the procedure severed the nerve fibers connecting the two hemispheres of the cerebral cortex, Sperry was able to research how each hemisphere of the brain specialized in processing. From Sperry's and other "split-brain" studies as they were called, it became clear that typically each hemisphere of the brain has its own specialties of thought. The left hemisphere specializes in language, signs, logical thinking, calculation, analysis (taking things apart) and linear processing (going step by step). The right hemisphere specializes in spatial patterns, symbols, holistic thinking, visual ideation, synthesis (putting things together), and imaginative conceptualization (expanding outside the box). In addition to its own specialties, each hemisphere appears to have very rudimentary capabilities for the other hemisphere's specialties as well. From these findings people began to describe themselves and others as "left brain" or "right brain" personalities, depending on which of the two types of thinking they were most gifted.

In the 1970s and '80s, Ned Herrmann conceived of different modes of thought occurring in various regions of the brain, in the higher level cortex and lower level limbic system. His Whole Brain Model comprised four quadrants of thinking styles linked to particular regions of the brain, with processes occurring on the left or right sides as represented here:

| | |
|---|---|
| A-quadrant | D-quadrant |
| Analytical, quantitative, | Intuitive, holistic, |
| logical, fact-based | integrating, synthesizing |
| B-quadrant | C-quadrant |
| Organized, sequential | Interpersonal, feeling-based |
| planned, detailed | kinesthetic, emotional |

In Herrmann's model, the four clusters of processing are typically available in each person, but one or more of the clusters is naturally dominant in a person's temperament, similar to Jung's theory. Through two decades of testing and applying his model to organizations, Herrmann amassed findings which indicate that the population is evenly distributed among these four types of thinking specialties. That is, 25% of the people show dominance in A-type analytical thinking, another 25% show dominance in B-type organized thinking, and so on around all four quadrants. This data suggests that groups and societies operate in such a way that each person's specialties of thought are balanced among the group as a whole. Although people are not all created equal, different styles of thinking appear to serve equally weighed roles in balancing each other to optimally achieve the group's common purposes. This generally fits with data in the 1970's by psychologists David Keirsey and Marilyn Bates. Their studies of married couples with Myers-Briggs testing showed an equal distribution among particular personality types: 25% were TJ's (favoring Thinking with Judging), 25% were FJ's (Feeling with Judging), 25% FP's (Feeling with Perceiving), and 25% TP's (Thinking with Perceiving). These Myers-Briggs types roughly equate to sides of the square Herrmann model (Herrman's AB side being TJ's, BC side FJ's, and so on). This data corroborates the understanding of thinking styles as a system in which each combination of thinking processes is offset and balanced by its corresponding opposite among the population as a whole.

In the 1980's Katherine Benziger modified Herrmann's model with new theories by neurosurgeon Karl Pribram.

Pribram suspected that the four different modes of thought were all processed in the uppermost cerebral cortex of the brain, but in its different quadrants of the left and right hemispheres' frontal and basal lobes. Although the locations of the processing were different from Herrmann's, her four-way model of modes of thought was similar:

| Front Left quadrant | Front Right quadrant |
|---|---|
| Analyzing, evaluating, making goals and decisions | Imagining, conceptualizing, generating holistic images |
| Basal Left quadrant | Basal Right quadrant |
| Sequencing, planning details, carrying out orderly routines | Harmonizing, synthesizing, associating expression and meaning |

Benziger's model, however, distinguished the right side modes so that it is easier to recognize them as thought processes which oppose those on the left. From this model, the present inventor noticed that the cutting process of analyzing opposed the connecting process of relating, and the opening process of conceiving opposed the closing process of order-setting.

Before returning to the development of the present invention, it is noted that in addition to those models already mentioned, there are now many other four-way models of temperament and personality in common use by psychologists and human development specialists. For example, the Learning Style Inventory developed in the 1970s by David Kolb uses a testing method to rate people's skills in four learning modes: Concrete Experience, Reflective Observation, Abstract Conceptualization, and Active Experimentation. From these scores, the test taker is classified as a Diverger, Converger, Accommodator, or Assimilator which relates to one's temperament. Team Resources, Inc. employs the DISC Profile System™ based on the theories of human behavior developed by psychologist Dr. William Marston in the 1920s and '30s. Through testing, the DISC model categorizes people into one of four types:

| Dominance (D type) | Influence (I type) |
|---|---|
| Driver, director | Expressive, persuasive |
| Competitive, blunt self-starter | Optimistic interest in people |
| Compliance (C type) | Steadiness (S type) |
| Conscientious, Cautious | Amicable, supporter |
| Analytical, orderly attention to detail | Easygoing, prefers security and routine |

Again a four-way pattern of diagonal opposition is evident in the descriptions of the four types in the DISC Model, but each DISC type reads like combinations of processes on sides of the Herrmann or Benziger models. Thus, the description of D type people in the DISC roughly equates to TP's in the Myers-Briggs system (I type=FP, S type=FJ, and C type=TJ). There are other such systems which categorize temperament, personality, or behavior into four categories that are identified by letters, words, and/or animal icons. Virtually all of these systems use individual written testing and scoring to determine one's personal style.

Other related methods and devices for typing personalities exist, yet none possess the unique characteristics of the present invention. U.S. Pat. No. 4,893,819, to Donald WRIGHT involves players in turn moving game pieces around a square playing pattern as determined by a roll of dice and gathering Feature Squares which characterize aspects of their personalities. Players gather squares by answering questions on cards with two answers reflecting a pair of opposing traits. When the first player has gathered one Feature Square in each of four categories, this player is then asked questions from each of four Choice Card decks to confirm that this player's personality type matches the Feature Squares he has claimed. If they match, this player wins the game, the winning player's personality is read from one of sixteen different Personality Type Profile Cards, and the game is over. Much like the Myers-Briggs Type Indicator (MBTI), in this game sixteen personality types are possible from the combination of four sets of opposing Feature traits (representing characteristics like Extroversion or Introversion, Judging or Perceiving, etc.)

By contrast, a preferred embodiment of the present invention categorizes players into one of four possible thinking styles (which are different from the sixteen MBTI personality types), and the game is not over until all players have learned something about themselves and others. All players using the present invention equally answer every question card drawn, each of which has four possible answers (corresponding to four thinking styles). Moves across the circular and radial playing pattern are made as responses to the questions without chance being involved. The present invention uses no dice. A player's movement toward one of the comers of the board portrays their generally consistent progression toward one of the four thinking style camps. On personal scoring sheets, players also can record each of their moves to generate a pattern of their answers which confirms their self-understanding. As each player eventually moves into the camp of their own thinking style, they then advance to a higher level of play which helps other players reach their own camps. While the WRIGHT invention plays like a conventional board game with players moving by chance and accumulating tokens toward one person winning the game, a preferred embodiment of the present invention has no winner, operates as an interactive group test, and is much simpler than the WRIGHT invention. The method of play of the present invention is not dependent on a subject theme, as the WRIGHT invention is associated with personality typing. Indeed, the method of the present invention can be used to categorize groups of players into a variety of possible four-way types, the four thinking styles being one example. The WRIGHT invention board game of individual self-discovery categorizes its single winner into one of sixteen possible personality types, whereas the present invention equally tests all players so that they all come to understand how the divergent styles among the group operate as a dynamic balanced system. With all players learning about each other through playing the game, the present invention can be instructional for group learning and team training, whereas the usefulness of the WRIGHT invention is limited to a game playing activity for the players involved.

U.S. Pat. No. 4,741,539, to John SUTTON et al. utilizes a hexagonal board and playing surface which is divided into six triangles representing six traits of personality: Tough, Tender, Stable, Changeful, Intellectual, or Emotional/Physical. Players place tokens in the triangular regions to predict the personalities of other players and themselves according to the traits listed on the playing surface within these regions. During the course of play, players take turns drawing cards with different questions having two answers, and they amass points and progress tokens as awarded by other players for their responses to the questions. The game is over when the first player has progress tokens across the outermost line of hexons in the triangular region of personality types nearest their predictor token and therefore wins the game.

A preferred embodiment of the present invention has no objective to win, no points or progress tokens are awarded, all questions are answered by all players without involving chance, no attempt is made to predict players' personalities, it portrays four different thinking styles rather than six personality traits, and the playing pattern is circular and radial within a square, not hexagonal as SUTTON's game. The present invention is unique because all players equally learn about themselves and others with their progress toward self-understanding represented both by (1) movement of a playing piece, and (2) a written tally of their moves on a personal scoring sheet. This scoring sheet allows players to take from the game a record of the various thinking styles that they favored. The objective of the SUTTON game is to amass tokens within a triangular region of the playing surface, whereas with the present invention, visual representation of progress toward a characteristic thinking style is indicated by movement of the playing piece toward a particular corner of the board. A fundamental difference is that the SUTTON invention is a conventional board game activity with a winning objective, whereas the present invention is an interactive group testing method with a key objective being the understanding of people's characteristic thinking styles and their differences.

U.S. Pat. No. 4,682,956, to Leonard KRANE is directed to a game in which two players at a time move their color coded game pieces, starting from a corner of a square board, around either of two alternate paths of movement: one as a square around the outer edge of the board, and the other as a single circle inside of and touching the square at four points. During play they roll dice to determine the number of spaces moved, land on color coded spaces which are color coded in eight colors corresponding to eight color coded sets of cards with seven questions on each side of each card, test their knowledge of each other by predicting and secretly recording how the other will respond to the true/false or the three-answer multiple-choice questions on these cards, and, upon proper prediction, are awarded Relationship Sticks that are inserted in color coded tokens representing the other player. The game is over when one of them (who is then declared the winner) has been able to insert at least one color coded Relationship Stick in each of four color coded tokens of the other. All of the color coding has to do with an eight-way distinction in "color personalities" as an application of the Luscher Color Test research that people of various personalities prefer different colors. These categorizations are not described in the abstract.

KRANE's game and preferred embodiments of the present invention are vastly dissimilar and have totally different objectives. For the present invention, the objective is not necessarily to win, no points or sticks are awarded, objects are not inserted in tokens to represent progress, more than two people can play, all questions are answered by all players without involving chance or a roll of dice, no attempt is made to predict and secretly record other players' responses, it portrays four different thinking styles represented by card suit symbols rather than eight "color personalities," and the playing pattern involves moving out from the center in a radial direction toward a corner, not around the board from a corner as in KRANE's game. Here again, the KRANE invention is a conventional game activity with a winning objective, whereas the present invention is an interactive group testing method with a key objective being the understanding of people's thinking styles.

U.S. Pat. No. 4,124,214, to Jesse PAVIS is directed to a game in which players start their game pieces from one of four corner spaces of a square board and move on a continuous main course around the periphery of the board (although other possible shapes are envisioned and a peripheral movement pattern is not the only possible route of the game course). Taking turns, they roll dice to determine the number of spaces moved then individually answer questions on cards that pertain to interpreting the meaning of dreams during various life situations. The multiple choice answers have different values (the possible interpretations being measured against the prevailing school of thought) such that the player is directed to move forward or backward various numbers of spaces. Thus the game board is treated as a scoring device. If a player lands on a corner square, then a corresponding corner card is drawn and all players answer that question and, after everyone has formed their answers, move according to its directions. The game is over when one player wins the game by reaching the last marker space on the game course. The theme of the game has to do with psychology, with board features labeled "Zodiac, Mythology, Symbols, Astrology, The Freudian Circle," etc.

Neither the subject matter of the questions, the method of play, the layout of the playing surface, nor the objectives of the PAVIS game are similar to preferred embodiments of the present invention. The PAVIS invention is a conventional game activity with a winning objective, whereas the present invention is an interactive group testing method.

U.S. Pat. No. 3,124,358, to G. H. WEEDMAN, is directed to a game in which players start their game pieces from a corner space of a rectangular board and move on a continuous track around the periphery of the board. Taking turns, they individually answer how to react to situations printed within the spaces on the playing track. Players respond to the situation by selecting an answer from a series of answer cards they have in their possession. Each reaction is rated on the basis of reasonableness of the choice as established by professional experts. The rating is displayed on an answer wheel disc mounted to the board, and by rotating the disc to his answer the player is told the number of spaces to be moved. There is an element of chance in both the situations and the responses, with the result that the player's score depends on a combination of chance and skill. The game is over when one player wins the game by reaching the last space having gone twice around the game track.

Neither the subject matter of the questions, the method of play, the layout of the playing surface, nor the objectives of the WEEDMAN game are similar to any embodiment of the present invention. The WEEDMAN invention is a conventional game activity with a winning objective, whereas the present invention is an interactive group testing method.

U.S. Pat. No. 4,877,254, to John YUSCAVAGE, is directed to a game in which players move from both ends of an S-shaped game course on a square board toward a finish space at the center to win. They roll dice to move and answer questions with answers on cards, challenged by a timing device. The questions pertain to a variety of subjects by categories. This game bears no resemblance to any embodiment of the present invention.

U.S. Pat. No. 5,156,407, to Christopher MOORE, is directed to a game in which players move from a start location along a rainbow shaped arc with four adjacent playing paths with varying degrees of difficulty to reach a pot labeled "success" and win the game. The four paths have different colors, as a rainbow, and question-answer cards which determine moves are color coded to these paths. The questions and answers pertain to diverse professions or career fields. This game bears no resemblance to any embodiment of the present invention.

U.S. Pat. No. 4,923,198, to Francisco DIAZ, is directed to a game which tests players' knowledge of geographical, historical, political, sociological, or other facts. In turns, players move according to a roll of dice and can move in either direction around a rectangular game course with a country map in the middle, answering fact-based questions on cards. The winner is the first player to correctly complete his scoring sheet based on his answers to the questions on the cards. This game bears no resemblance to any embodiment of the present invention.

SUMMARY OF THE INVENTION

The present invention is directed to a method and device for characterizing thinking styles. In developing the present invention, it was observed that the symbols for playing card suits remarkably represented the four types of thinking processes suggested by the Herrmann and Benziger models. Not wishing to be bound by theory, the suits seemed to be deep, subconscious archetype images hinting at the human mind's organization of divergent sets of thinking processes into a self-balancing system. If this were so, indeed, the card suits could offer further understanding of these varied processes. The representation of the suits by colors (the spade and club icons in black with the diamond and heart in red) portrays the specialization of thinking processes in the brain's left hemisphere (black suits) and right hemisphere (red suits).

Left Hemisphere: The spade evolved from the sword of the Tarot deck, and it portrays the cutting, segmenting process of analysis which narrows information to a singularity, such as in making decisions and establishing goals. The club is a series of rounded shapes closed in on themselves fortresslike that is characteristic of procedures (daily routines, laws, traditions) which are sequences of steps that people have established to minimize ongoing analysis. Both the spade and the club are grounded on stems representing that analysis and order-setting are the most conscious of a person's processes, are applied to language, and tend to be the basis of a person's grounded reality. The sword and the club are also weapons of power, of offense and defense. The spade and club processes typically overwhelm the subtle, mysterious right hemisphere processes of which people are less aware and have limited conscious control over their operations.

Right Hemisphere. The diamond icon is the multi-faceted representation of a crystal which refracts light, breaking it into multiple rays, as does a person's imaginative conception in opening and expanding a range of possibilities. The heart is a symbol for love and caring connection of two or more in relationship. The diamond and heart symbols do not have stems but, with points on the bottom, seemingly dangle in space. This lack of stems to ground them portrays the inexplicable ways in which ideas arise as if from out of the blue without conscious effort and a person's attraction to relationships which feels like a tug of the heart without a person's willful ability to control it. These right hemisphere specialties of thought have spontaneous, whimsical, spirited, soulful qualities to them that seem the antithesis of analytical, orderly grounded reality.

The card suit symbols oppose each other in pairs as do the contrasting types of thinking processes. The spade is the heart shape turned upside down and opposite in color, as the cutting process of analyzing opposes the connecting process of relating. One might think of the open diamond process of conceiving as the closed, order-setting club having been blown inside out. When the symbols are arranged at diametric opposite corners in a square or rectangle, the processes can be combined with each other from corner to corner of the square or rectangle, but diagonally they are opposites and mutually exclusive. Thus people may enter into states of mind in which they are both conceptual and analytical, orderly and analytical, or any combination around the sides of the square. Yet it is exceptionally difficult to be both coolly analytical and warmly relational at the same time, or to hold to existing order while conceiving anew. These opposing attributes present people with choices they make, both within themselves and in groups and society as a whole.

The model of thinking processes for the present invention is arranged in a back to front variation of the Herrmann and Benziger models, because perceptual input information is processed in the rear lobes of the brain and operational output instructions and procedural planning are specialties of the front lobes. However, there is relatively less emphasis in the present invention on where these processes occur in the brain as there is on how groups of people operate as a system by their favoring particular processes or combinations of them.

The research by Herrmann (and also by Keirsey-Bates) suggests that each of the four kinds of thinking processes symbolized by the card suits in the present invention is equally represented in human society and, by inference, equally necessary to life as a self-organized system which evolves at a safe, balanced rate of growth. Written testing and scoring by both the Herrmann and Benziger methods confirms patterns of thinking styles that are evident in people playing the board game embodiment of the present invention. People usually show a marked preference for one of the four processes, secondary usage of the two processes at the corners neighboring their dominant process, and little usage of the process diagonally opposite their dominant process. This pattern is like a boxer in one corner of a boxing ring with arms on the ropes out to neighboring corners, but with an opponent standing at the far corner. Groups of people tend to break into opposing camps of thought, with equal quarters of the population upholding each of the four divergent perspectives on life, like groups of boxers in all four corners. Each of the four camps have different basic interests, priorities, standards of behavior, ways of thinking, etc. that are driven by their favored types of thinking. These varied styles, summarized in Detailed Description of Preferred Embodiments of the Invention, are the basis for the four categories of equally weighted answers in the game embodiment of the present invention.

The present invention is achieved by the provision of a method of categorizing participants into categories which categories are characterized by personal characteristics, the method comprising presenting a question to a group of participants to which question each participant provides a subjective answer selected from a predefined group of answer choices, wherein each choice is equally subjectively valid and wherein in response to each answer choice participants concurrently make visible progress toward a category. Preferably, each of the categories is represented by an answer choice. Preferably, the answer choices are grouped in pairs, each pair representing two contrasting characteristics. In preferred embodiments, the categories are selected from the group consisting of thinking styles, personality characteristics, learning styles, work skills, movie preferences, sexual drives, and combinations thereof. Preferably, progress toward a category is monitored and recorded essentially concurrently with the progress. Preferably, such monitoring and recording is visually represented. Preferably, the monitoring and recording is selected from the group consisting of movement of a playing piece or marker across a playing surface, written record portrayed on a visual pattern, and combinations thereof. In preferred embodiments the foregoing method further comprises a game with at least one objective, which preferably comprises learning. Preferably, the progress is indicated by moving playing indicators on a game board. In other preferred embodiments, the progress is indicated by the movement of indicators on a game associated with an electronic computer chip. In still other preferred embodiments, the progress is indicated by the movement of indicators on an internet device. In still other preferred embodiments, the progress is indicated by the movement of playing indicators on a television game show.

The present invention is further achieved by the provision of a method of categorizing participants into categories which categories are characterized by personal characteristics comprising repeating the foregoing method until a participant may be identified as being a member of a category.

The present invention is further achieved by the provision of a board game played by practicing the foregoing method.

The present invention is further achieved by the provision of a game played in association with an electronic computer chip, which game is utilized by practicing the foregoing method.

The present invention is further achieved by the provision of an internet device utilized by practicing the foregoing method.

The present invention is further achieved by the provision of a television game show played by practicing the foregoing method.

The present invention is further achieved by the provision of a board game for categorizing participants into categories, which categories are characterized by personal characteristics, the board game comprising a game board, the game board comprising a central portion and a peripheral portion, the peripheral portion having a plurality of distinct points associated therewith, each of the plurality of points representing a personal characteristic; playing indicators; wherein play proceeds by movement of the playing indicators in a generally outward manner from a starting position associated with the central portion in a direction of movement generally toward a point on the peripheral portion; and wherein movement is generally determined by subjective answers to questions, each of which answers correspond to the distinct points associated with the periphery. Preferably, the playing indicators comprise mechanical playing pieces. Preferably, the generally outward manner comprises a generally radial direction. In other preferred embodiments, the generally outward manner comprises a generally circular direction. Preferably, the plurality of distinct points comprise at least four distinct points, which preferably represent at least four thinking styles. Preferably, the at least four thinking styles comprise stabilizers, unifiers, identifiers, and expanders. Preferably, the at least four thinking styles are represented by clubs, hearts, spades, and diamonds.

BRIEF DESCRIPTION OF THE DRAWINGS

The foregoing and other objects, features, and advantages of the invention will be apparent from the following more particular description of the preferred embodiments, as illustrated in the accompanying drawings, in which reference characters refer to the same, or like, parts throughout the various views, and wherein:

FIG. 4 is an illustration of game cards in accordance with a preferred embodiment of the present invention.

FIG. 6 illustrates a guide to the four thinking styles according to a preferred embodiment of the present invention.

DETAILED DESCRIPTION OF PREFERRED EMBODIMENTS OF THE INVENTION

Figure 1:
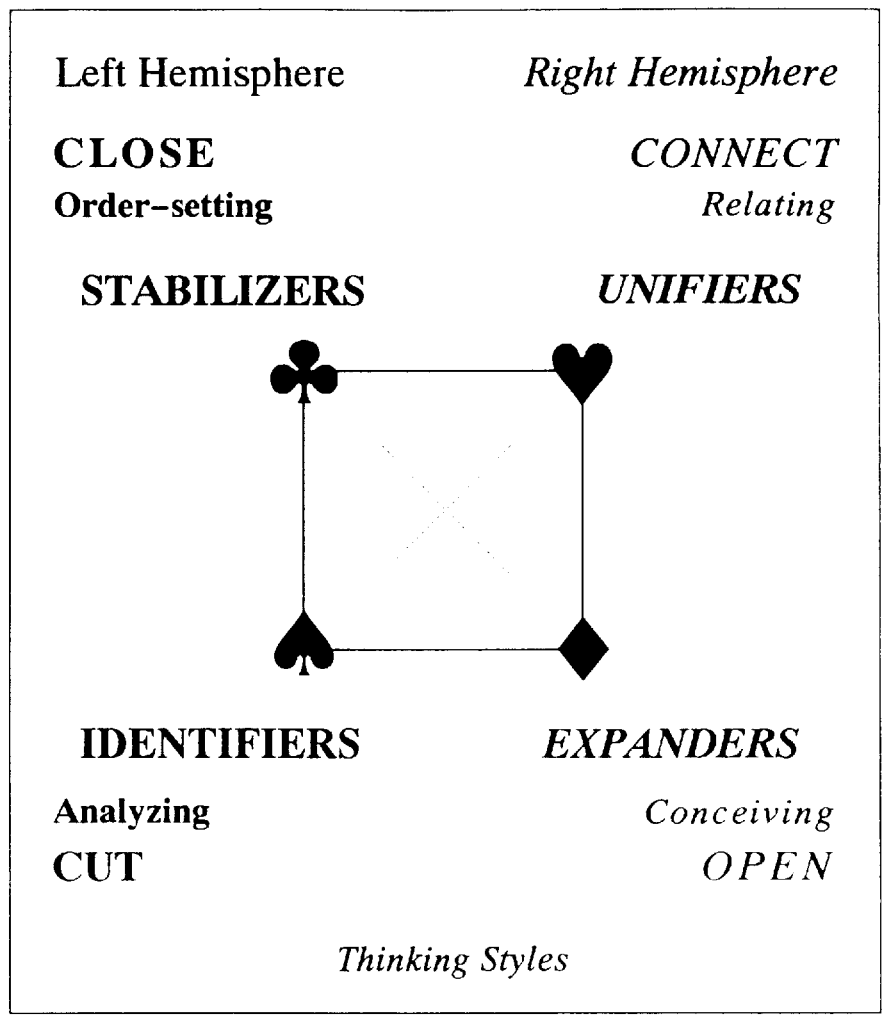
FIG. 1 is an illustration of a graphical depiction of the theoretical model of the present invention, showing the interrelatedness of the four types of thinking styles.

Although not wishing to be bound by theory, the present invention is based on a theoretical model for characterizing thinking styles types into four basic classes. The model lends itself to the present invention, which is methods for characterizing individuals or groups of people into different classes. A preferred embodiment comprises the use of a board game which facilitates the aforementioned classification and categorization.

In accordance with the present invention, the game is an interactive group testing device that, in a fun way, sorts players into four sub-groups (or camps) and visually portrays their progression into these camps as players respond to a series of questions, all of which have four equally valid answers that have been uniformly categorized as to type. The questions are worded to elicit a player's consistent tendency to utilize a particular style (or styles) of thinking processes from among four possible types, and the game with its four-way movement pattern records and displays these preferences. (However, the game device could alternatively be applied to any group sorting task by wording the questions to a different topic, such as typing by personality styles, or movie preferences, or sets of work skills, etc.) Often players are unaware of their proclivity to display such tendencies, and the game makes them evident so that they can be understood and discussed among the group. Usually such type categorizing has been done by personal testing in which participants record answers in writing to questions for later scoring and explanation by an expert. In contrast, the game device of the present invention enables the type categorizing to be revealed in an open, forthright way by a group of players for their joint discussion and interpretation. By this device's method of engaging the participants in a game and cleverly wording questions to begin on an innocent theme, the participant's defenses against disclosing such personal traits are broken down. While playing the game, all participants reveal characteristic aspects of their thinking to other members of the group, and they see how their differing styles fit an overall pattern which becomes evident during the course of play. While an individual written testing approach tends to reinforce defenses and promote self-discovery by private reflection, this game device displays the pattern of people's differences in a way that enables members of the group to comprehend their equally valid points of view in open forum. Therefore, this game can be a tool for identifying people's natural oppositions and then prompting discussions which can help ease personal animosities and reduce chronic conflicts. This self-understanding and awareness of natural opposition within the group can take place in the home or office without involving paid experts trained in human psychology.

The symbolization of the various thinking styles by the card suits (spade, club, diamond, heart) promotes easy understanding of their characteristics in an equally valued, non-pejorative fashion.

FIG. 1 schematically represents symbols of the four basic classes of thinking styles arranged at diametric opposite corners in a square or rectangle in accordance with the present invention. Each of the four thinking styles is linked to different types of thinking processes which serve a particular greater purpose to a group or society. The identifiers, who are skilled in the analyzing type of thought, tend to be good at obtaining and breaking down information, cutting it into separate bits, making decisions on their findings, setting goals, and thus identifying an independent course or direction for the group. The unifiers, who are skilled in the relating type of thought, are often good at rallying people to team together around a common cause, building a commonality of purpose, connecting people to work and act in harmony, and thus unifying individuals into cohesive groups such as families, church congregations, governing bodies, etc. The stabilizers, who are skilled in the order-setting type of thought, tend to be good at setting up the routines and procedures for the group, promoting rules and laws, providing institutional structure, limiting the speed of chaotic change so that it will not overwhelm the group's ability to survive, and thus stabilizing the group to operate within a range of safety. The expanders, who are skilled in the conceiving type of thought, are often good at imagining and envisioning new ways for the group to function and do things, adjusting its role in the world at large, opening and enlarging the group's level of awareness and acceptance of these new ways, and thus expanding its growth into the future in defiance of old procedures. With such varied greater purposes, all four thinking styles serve equally necessary roles for the well-balanced success of any group.

Various aspects of these four thinking styles are shown in FIG. 1 and further elaborated in tabular form in FIG. 6.

Figure 2:
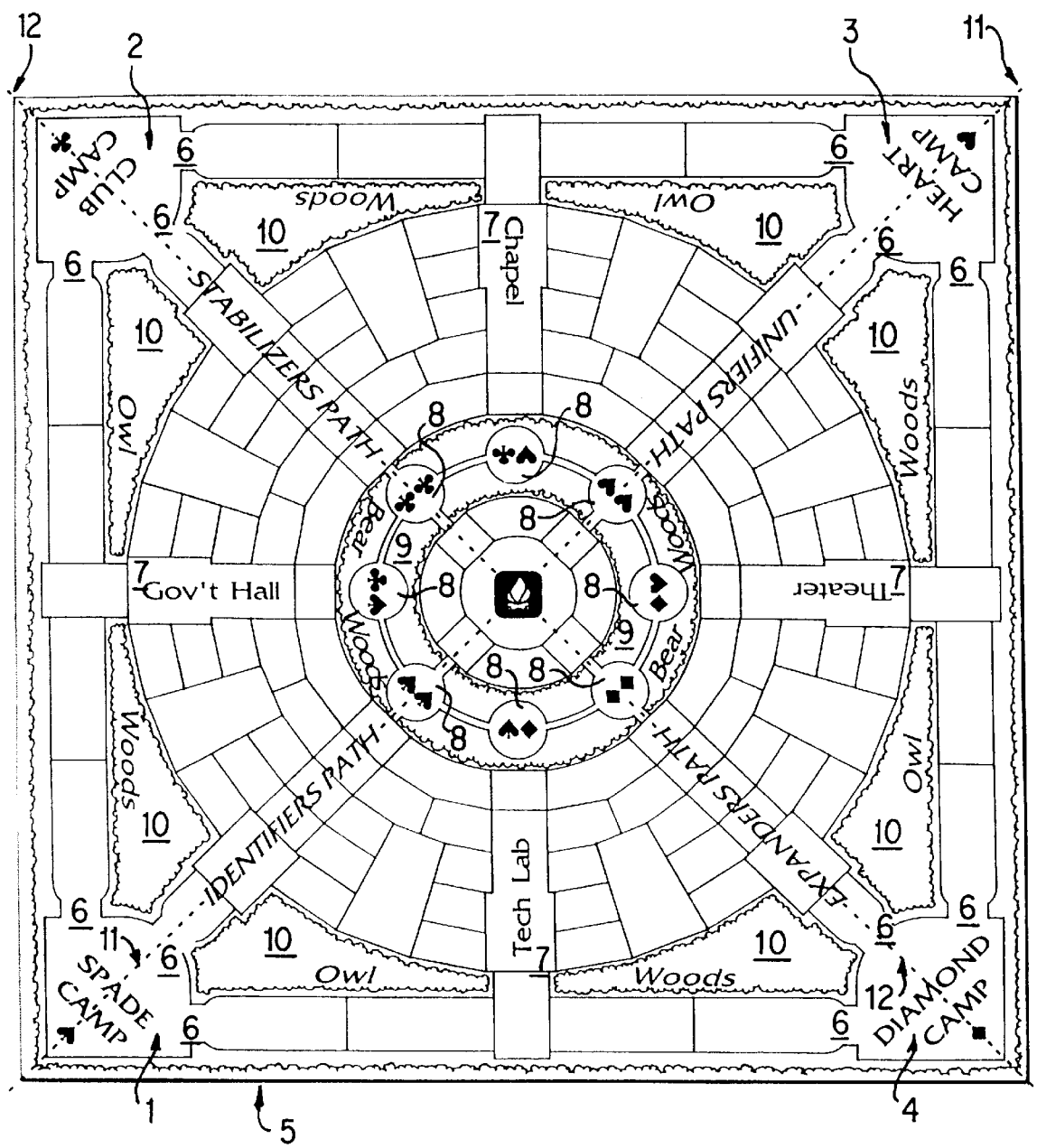
FIG. 2 is an illustration of a game board in accordance with a preferred embodiment of the present invention.

As the thinking processes (or modes) can be classified as two sets of opposing operations, the crossed, double-axis design of the playing surface as shown in FIG. 2, effectively portrays the paradoxical manner in which they often work at cross purposes yet are equally necessary and function together as an integrated system. The crossed axes are shown as dotted lines 11 and 12 in FIG. 2. This combination of the symbolic representation and the pattern of their axial locations on the playing surface makes it easy for people to see the holistic interrelationships between divergent types of thinking (or camps of thought) to which people are variously predisposed. By awarding badges to players as they reach their camps, members of the group have a means of associating their friends and family members with the camps for more effectively learning the styles.

In accordance with preferred embodiments of the present invention, the design of the game's playing surface allows players to independently move toward any of the four sub-categories in response to successive questions as they move outward toward classification. The movement of the game piece across the playing surface depicts the classifying operation while it is taking place. In addition, a self-scoring sheet allows each player to record their moves according to suit. This supplemental indicator allows them to see by their responses that they have rather consistently favored certain types of thought processes (or other aspects of themselves that can be similarly classified).

Because all four thinking styles are equally valid and necessary to the group, the game has no winner in preferred embodiments. All players benefit from play. Play ends when all players have progressed into their camps and sufficient group learning has occurred. Players of a particular thinking style may compete to be first to reach their camp, however this approach is not the only way to play the game. Indeed, varied attitudes toward playing the game are essentially the same as the varied approaches of different camps of thought toward experiencing life.

A higher level of play that occurs after players have reached their camps gives them practice in understanding the thinking of people with different styles. This represents the wisdom that comes in accepting people of all styles and recognizing their contributions to the group even though they may think and act differently from oneself Practicing the attitudes of the varying camps opens people to consider how and why another's views may oppose their own. This second level of play also provides players with something interesting to do until all members of the group have reached their camps and the group as a whole decides to end the game.

The way in which all of these features have been integrated makes the game embodiment of the present invention a highly efficient, interactive group testing device for identifying and easily explaining people's different thinking styles. The innovative method of the game includes the combination of:

Four-way movement pattern of the playing surface which correlates with four equally valid answers to all questions.

Crossed axial layout (axis 11 and axis 12 of FIG. 2) of the major paths in the game to represent the opposition inherent in the differing styles.

Symbolization of the four styles by the card suits.

Combination of self-scoring plus visual representation of the sorting process by progression of the game piece.

Badges for personal association with the four styles.

Two levels of play with different kinds of objectives.

Non-competitive method of play with a group-determined finish.

The foregoing specific embodiments are illustrative of applications in which the present invention can be employed. Those of ordinary skill in the art will readily understand that other embodiments are suitable and are in accordance with the present invention as well.

Without further elaboration, it is believed that one skilled in the art can, using the preceding description, utilize the present invention to its fullest extent.

The following working examples are, therefore, to be construed as merely illustrative, and not limitative of the remainder of the disclosure in any way whatsoever.

WORKING EXAMPLES

Example 1—"Camp Paradox" Board Game

Game Purpose: Education (self-discovery and learning about others in the group) for understanding players' thinking styles and temperament.

Player Ages: Adult is preferable. Not especially suited to children and adolescents whose mature thinking processes have not yet coalesced.

Basis: The game is founded on psychologist Carl Jung's four functions of the mind, updated for recent discoveries. The cards ask questions with four choices that each pertain to different types of thinking. This game tests and categorizes individual thinking styles in an interactive group game session.

Theme: The setting is hypothetical "Camp Paradox." The players are new summer campers who must find their way to one of four different base camps where they will be most comfortable with like-minded campers.

Equipment:

Board—Printed surface on cardboard backing approximately 22" square.

FIG. 2 illustrates a preferred embodiment of a "Camp Paradox" game board.

Each of the four corners, 1, 2, 3, and 4 of the game board generally designated as 5 is associated with a particular category of thinking style in accordance with the present invention. Thus, in the embodiment of FIG. 2, corner 1 is associated with the "Spade Camp" toward which "Identifiers" (analyzing thinking style, keyword "cut") will progress during play; corner 2 is associated with the "Club Camp" toward which "Stabilizers" (order-setting thinking style, keyword "close") will progress during play; corner 3 is associated with "Heart Camp" toward which "Unifiers" (relating thinking style, keyword "connect") will progress during play; and corner 4 is associated with the "Diamond Camp" toward which "Expanders" (conceiving thinking style, keyword "open") will progress during play.

Figure 3:
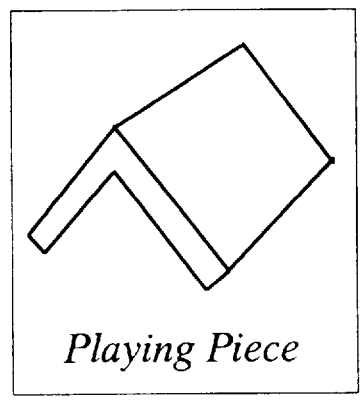
FIG. 3 is a schematic illustration of a playing piece in accordance with a preferred embodiment of the present invention.

Playing Pieces—8 variously colored wood or plastic angles, approximately ¾" in size, representing tents. FIG. 3 illustrates a preferred embodiment of a playing piece in the shape of a tent.

Game Cards—Several categories of cards with questions or instructions. Preferably, cards are sized 2½"×3½". FIG. 4 illustrates preferred embodiments of four different cards, two of which are "Bear Quest" cards (top of FIG. 4), the bottom two are "Owl Mission" cards.

Card Holder—A small, cardboard box that holds the cards so that answers (on back of cards) are hidden from view until turned over by the reader.

Figure 5:
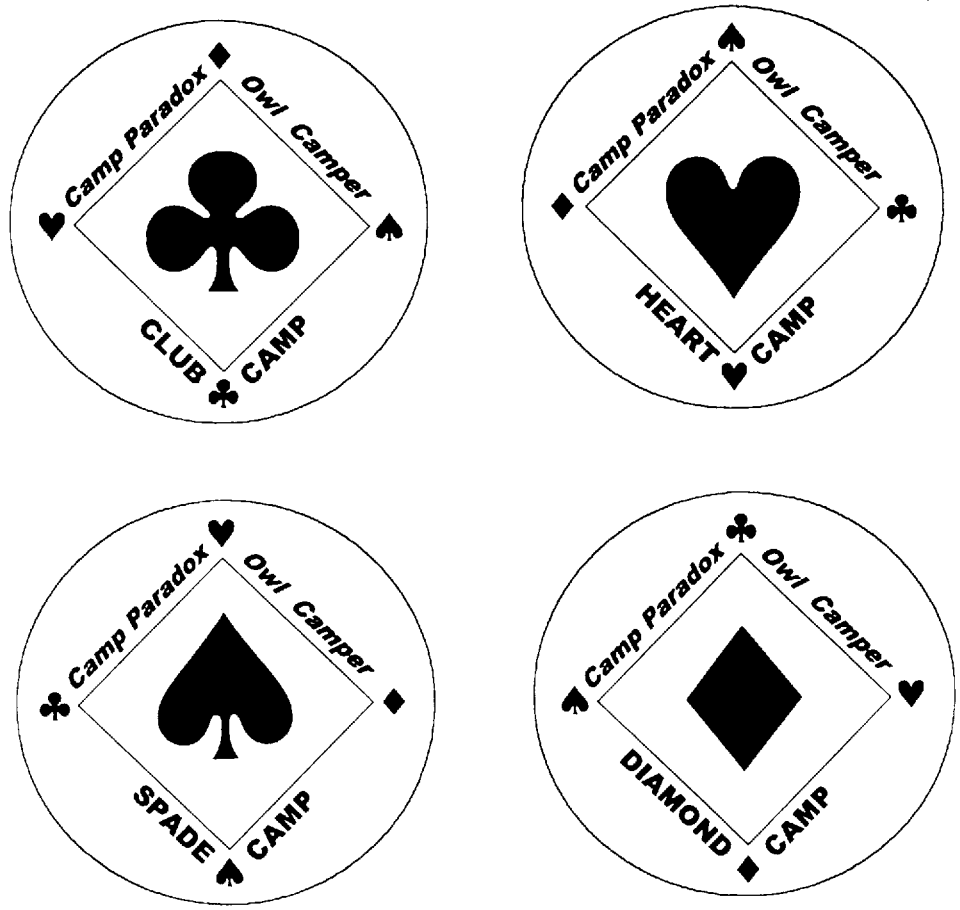
FIG. 5 is an illustration of camp badges in accordance with a preferred embodiment of the present invention.

Badges—Campaign-style pin-on badges honor a player's advancement from "Bear class" camper to "Owl class" camper. These badges designate the type of thought processes applicable to the majority of answers given by that player, thus indicating the player's basic thinking style. FIG. 5 illustrates preferred embodiments of the four types of "Owl class" badges.

"Camp Guide Book" —Handout summarizes divergent characteristics of thought processes, represented by a card suit symbol for each camp. FIG. 6 illustrates information which is preferably presented in a "Camp Guide Book."

Figure 7:
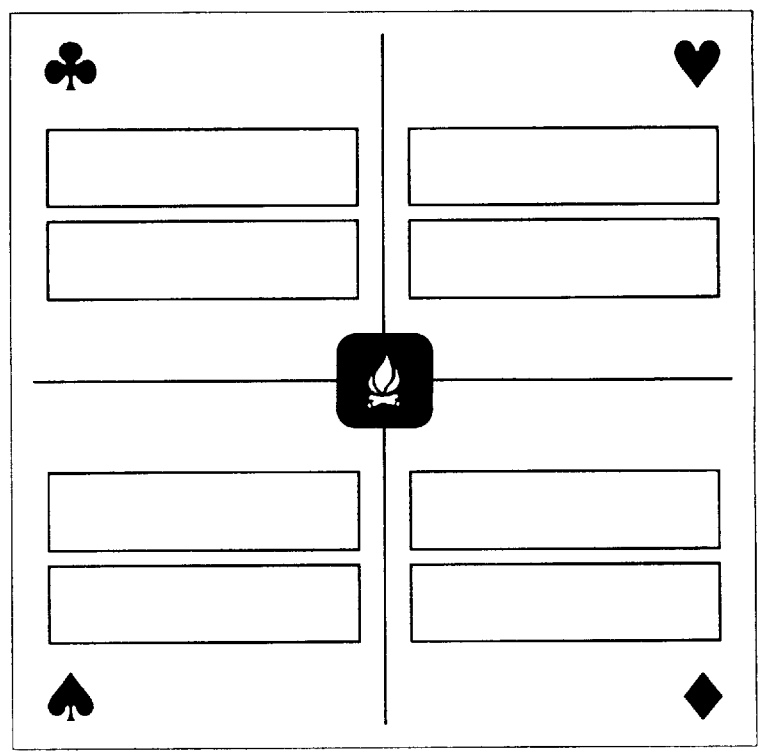
FIG. 7 illustrates a personal scoring sheet in accordance with a preferred embodiment of the present invention.

Personal scoring sheets—Sheet for tabulating moves by suit. The scoring sheet acts as a record of the players' experiences. FIG. 7 illustrates an example of a preferable Personal Scoring Sheet.

Basic Play ("Bear Level"):

Players start by placing their tent game pieces on their own choice of one of eight circular "Groves" 8 in "Bear Woods" 9. Players are then ready to begin answering questions which allow them to move through camp as novice "Bear class" campers. (Optional Start: Players answer pre-qualifying questions to determine the Grove that is to be their starting place, or they all start at the center of the game board.)

The primary objective is for each player to move outward to one of four "Base Camps" in the corners 1, 2, 3, and 4, of the board (designated Spade, Diamond, Club and Heart Camps) where like-minded "campers" camp. Achievement of this objective constitutes a typing of the thinking style of the player who has achieved that objective, as is discussed herein. As all players of the game are typed the group is separated into subgroups, each subgroup corresponding to a camp which in turn, corresponds to a thinking style. In the previous example, four subgroups were resolved, or separated out. Other embodiments could have greater or fewer subgroups. When a player is admitted into one of these Base Camps, the player becomes an "Owl class" camper with new objectives (described later under "Owl Level" play).

In turns, players draw and read "Bear Quest" cards. Each card has a question with four possible answers which are all valid, but each answer differently appeals to varied styles of thinking. The player drawing the "Quest" card reads it, and all players individually decide how they would respond to the question. After each player has settled on their own answer, the reader turns the card over and gives the move instructions for each of the four possible answers. Depending on each player's own response, they move their tent one space toward either Spade, Diamond, Club or Heart Base Camps. All players answer and move their tents for each "Quest" card drawn. The used card is returned to the back of the deck, then the next player in turn draws and reads a card. (FIG. 4 illustrates samples of cards.)

Tents may be moved around rings or along axial paths, taking the shortest route to the designated suit. Players move one space at a time, typically in an outward axial direction or sideways along a ring. As most individuals tend to favor one (or two) of the four types of thinking processes due to their own nature and nurture, they usually will consistently move toward a suit (or suits) representing their dominant type(s) of thinking.

On personal scoring sheets (see FIG. 7), players record their own moves by suit to form a graphic depiction of the types of thinking processes that they favor. By the end of the game, the pattern thus revealed offers a tool for self-discovery of their preferred thinking style and its characteristic traits which are summarized in the Guide Book.

A player may not move either outward or inward from ring to ring except on the diagonal path aligned with that suit's Base Camp.

If a player moves through one of the four career fields 7 midway at the sides of the board (Tech Lab, Government, Chapel, or Theater), the player progresses in a rectilinear direction along the outer path beyond "Owl Woods" 10. In this area, the search is narrowed to just two Base Camps.

Upon passing through the gateway 6 to a Base Camp, the player moving into that Camp is awarded an Owl Camper badge of the Camp being entered. Thereafter during his turn, this "Owl class" Camper draws from a different deck of cards and moves by different laws (see "Owl Level" play), while "Bear class" players who have not yet become Owls continue with simultaneous "Bear Level" play during their turns.

Advanced Play ("Owl Level"):

"Owl class" players draw from "Owl Cards" during their regular sequence in turn with the other players. Owl Cards obligate the player to temporarily adopt the thinking style of a particular Camp in responding to questions with two opposing answers.

As the Owl camper draws a card instructing him to be, for instance, a Heart Camper, he moves his tent to Heart Camp and is, therefore, in general alignment with Bear campers on their way to Heart Camp. If the Owl correctly answers the question on the card as typically would a Heart Camper, then all Bear campers may move one space either toward or away from the Owl. The Owl thus possesses a certain magnetism to help Bears reach their intended Base Camp and become Owls as well.

The objective of the game is for all players to reach their respective Base Camps, become Owl campers, sample Owl Level play, and learn about their own and each other's thinking styles from the Camp Guide Book. The game is ended by player consensus or a moderator's instructions.

Uniqueness: Features which make this game unique are:

Everyone benefits from play. The foundation of the game is educational; and its objectives are also cooperatively, not only competitively, driven.

There are no right or wrong answers, but only the personal views of the players. The game conveys the value of diverse viewpoints to round civilization into balanced wholeness.

Personal discovery. The game moves the topic of thinking style and temperament from the realm of individual written testing out into an open, interactive group arena—allowing co-workers, families or couples, for example, to understand an underlying basis for actions which might have caused disagreement.

Card questions categorize thought processes. The game sorts players' responses into representations of analyzing and conceiving perceptual processes plus ordering and relating operational processes. (Analyzing and relating oppose each other, as do conceiving and ordering.)

Four-way movement pattern. The game board serves each player in seeking the Camp which is their own goal. All have equal validity and equal movement patterns to reach them, encouraging independent thinking.

Plural playing patterns. The board and game equipment accommodate both Bear Level and Owl Level play, symbolizing degrees of awareness about a player's natural thinking style and the thinking styles of others.

No game-determined finish. As Owl Level play can continue for some time, multiple games in seminars may operate simultaneously. (No players are "finished" and idling in wait for others to complete play.)

Camp theme. The summer camp motif transports players back to the innocence of childhood when people are more naturally themselves. In addition, the Base Camps signify the ways people often form into opposing camps such as Republicans vs Democrats, science vs religion, Washington vs Hollywood, way out designers vs up tight bean counters, analytical managers vs relational union interests, etc.

In addition to a board game embodiment, other preferred embodiments of both the game and the method are within the scope of the present invention as well. In particular, method aspects of the invention can be practiced on any suitable medium, such as a game board as discussed above, electronic games or constructs, life-size playing fields, indoor or outdoor camp-like settings, etc. Electronic games and constructs and computer games are common in that use is generally associated with an electronic computer chip. Suitable media will be readily apparent to those of ordinary skill in the art. Thus, other preferred embodiments of both the method and the game of the invention include, but are not limited to, an actual indoor or outdoor camp or camp-like setting with a "life size" version of the game board where either the players themselves or playing pieces occupy the game board or an electronic game or construct which is played on a computer-generated playing surface with questions built into and posed by its software and markers automatically move across the playing surface by players' answers input into the computer. Other preferred embodiments include an internet or other computer operation in which the players may be physically distant but learn about each other by means of a software application embodying the method. Other preferred embodiments include a game show which is broadcast, such as a television game show in which participating players answer questions and move themselves physically or by mechanical or electronic representation across a playing surface wherein the surface is arrayed in accordance with the invention as exemplified herein.

In each embodiment of the present invention, a participant's progress is visually represented. Visual representation can comprise the movement of playing pieces or indicators on a board game, the movement of an electronic display or indicator, or electronically illuminated, activated, or enhanced region of an electronic display, such as an LCD, LED, etc. Other visual representation comprises the actual movement of people across a life size game playing surface, such as on a television game show, or in an actual camp-like setting. Alternatively, the progress may not be displayed at all times, but may be displayed when desired. For example, the game may be played in remote locations by individual players, such as on the internet, with progress displayed in response to requests by the players.

Questions posed in accordance with the present invention can relate to a variety of different themes. Preferred themes include, but are not limited to, thinking styles, personality characteristics, learning styles, work skills, and sexual styles. Each of these themes may be divided into pairs of opposites. For example, thinking styles may be divided into the categories which include stabilizers, identifiers, unifiers, and expanders, wherein stabilizers and expanders are opposites, and identifiers and unifiers are opposites. Work skills may be divided into the categories which include proceduralists, analysts, sellers, and visionaries, wherein proceduralists and visionaries are opposites, and analysts and sellers are opposites. Other themes can be selected in accordance with the present invention.

In preferred embodiment of the present invention, the playing pattern may have two or more sets of opposites such that the total number of opposite traits will equal the number of answer choices to questions and also the number of sides to the playing pattern. For example, in a preferred embodiment, two pairs of opposing traits yields four opposites portrayed on a four-sided square playing surface with objective spaces in the outside corners. In alternative preferred embodiments, three pairs of opposing traits yields six opposites portrayed on a six-sided hexagonal playing surface. In still other preferred embodiments, however many pairs of opposing traits are represented, the number of objective spaces in the outside periphery of the playing surface will be twice the number of pairs of traits. Other embodiments are within the scope of the present invention as well.

In preferred embodiments of the present invention, depiction of individual participants' responses and progress toward the objective may be by movement of a playing piece or marker across a playing surface. In other preferred embodiments of the present invention, depiction of individual participants' responses and progress toward the objective may be demonstrated by a self scoring record of participants' answers by categories portrayed on a visual pattern consistent with the present invention. In still other preferred embodiments, a combination of the foregoing can be combined, such that there is both movement of a marker piece and a record of the movements.

In preferred embodiments, an objective may be to learn, such that there is no winning purpose, and the game is over when all players have reached an objective. In other preferred embodiments, an objective may be to win, such that the first player to reach the objective is considered the winner and thus ending the game.

Figure 8:
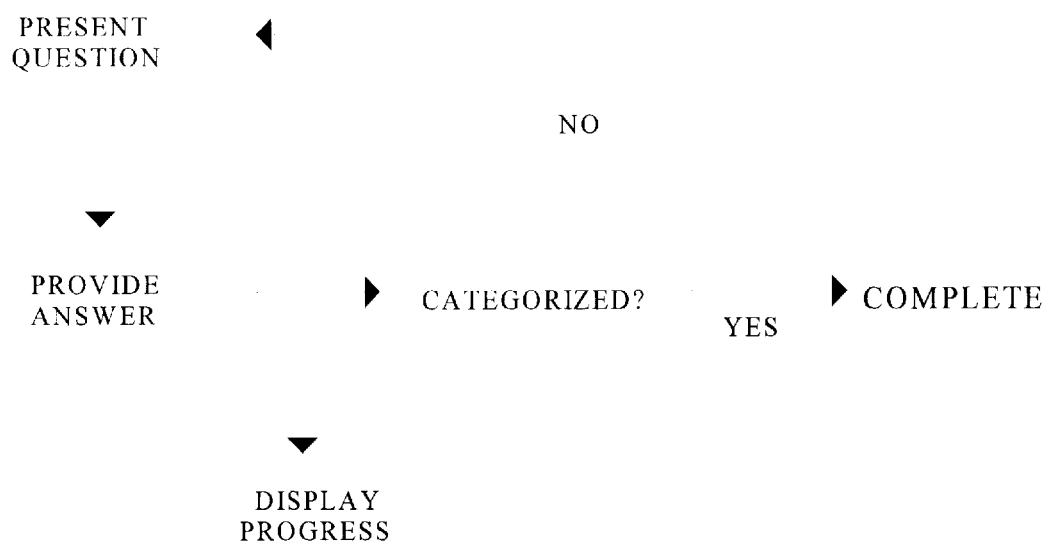
FIG. 8 is a schematic representation of a method of the present invention.

As discussed above, the invention also involves method aspects. Essential elements of a preferred method embodiment of the present invention may be schematically illustrated in the form of the flow chart diagram, shown in FIG. 8. The method illustrated involves categorizing or typing participants into categories of thinking styles. The categories include aspects of personal characteristics. The method comprises presenting a question to one or more participants to which question each participant provides a subjective answer selected from a predefined group of answer choices, wherein each choice is equally subjectively valid and wherein in response to each answer choice participants concurrently make visible progress toward a category. Preferably, a group of participants is asked a single question, although the invention is not limited to this. For example, a group could be split into separate portions and the separate portions may be asked different questions. Alternatively, random samples of a group could be presented with a single question. This process is repeated until a sufficient number of participants or subjects have progressed far enough toward a particular camp to be characterized as having been "typed." Preferably, "typing" occurs when a participant has arrived at a particular camp or an area associated with a particular camp.

From the foregoing descriptions, one skilled in the art can easily ascertain the essential characteristics of this invention, and without departing from the spirit and scope thereof, can make various changes and modifications to the invention to adapt it to various usages and conditions.

Although the invention has been described with reference to particular embodiments, it is to be appreciated that various adaptations and modifications may be made and the invention is only to be limited by the appended claims.

The entire disclosures of all patents and publications, cited above and below, are hereby incorporated by reference as though set forth in full herein.

What is claimed is:

1. A board game for categorizing participants into categories, which categories are characterized by personal characteristics, said board game comprising:

a game board, the game board comprising a central portion and a peripheral portion, the peripheral portion having a plurality of distinct points associated therewith, each of the plurality of points representing a personal characteristic; and playing indicators and a question and answer indicating system;

said game board comprising a plurality of spaces defining annular and radial paths; and said central portion being associated with a starting position;

wherein said playing indicators are moved in a generally outward manner from said starting position in a direction of movement generally toward one of the distinct points on said peripheral portion in response to questions posed to a game player; and wherein the direction of movement is generally determined by subjective answers to the questions posed to the game player, each of which answers correspond to one of the distinct points associated with the periphery.

2. The board game of claim 1, wherein said playing indicators comprise individual playing pieces.

3. The board game of claim 1, wherein said generally outward manner comprises a generally radial direction.

4. The board game of claim 1, wherein said plurality of distinct points comprise at least four distinct points.

5. The board game of claim 4, wherein said at least four distinct points represent at least four thinking styles.

6. The board game of claim 5, wherein said at least four thinking styles comprise stabilizers, unifiers, identifiers, and expanders.

7. The board game of claim 5, wherein said at least four thinking styles are represented by clubs, hearts, spades, and diamonds.

8. A board game for categorizing participants into categories, which categories are characterized by personal characteristics, said board game comprising:

A) a game board, the game board comprising:
   a central portion associated with a starting position, and
   a peripheral portion, the peripheral portion having at least four distinct points associated therewith, each of the at least four points representing a personal characteristic;
   a plurality of spaces defining annular and radial paths; and B) playing indicators and a question and answer indicating system;

wherein said playing indicators are moved in a generally outward manner from a starting position associated with said central portion in a direction of movement generally toward one of the at least four points on said peripheral portion in response to questions posed to a game player; and wherein the direction of movement is generally determined by subjective answers to the questions posed to the game player, each of which answers correspond to one of the at least four distinct points associated with the periphery.

9. The board game of claim 8, wherein two of said at least four points are disposed at opposite ends of a first axis, and two of said at least four points are disposed at opposite ends of a second axis, and said first axis and said second axis intersect at said central portion.

10. The board game of claim 8, wherein said generally outward manner comprises a generally radial direction.

11. The board game of claim 8, wherein said at least four distinct points represent at least four thinking styles.

12. The board game of claim 11, wherein said at least four thinking styles comprise stabilizers, unifiers, identifiers, and expanders.

13. The board game of claim 11, wherein said at least four thinking styles are represented by clubs, hearts, spades, and diamonds.

* * * * *